United States Patent [19]

Uhrig et al.

[11] Patent Number: 5,100,989

[45] Date of Patent: Mar. 31, 1992

[54] RESIN ACID ESTERS BASED ON NOVOLAK OXYALKYLATES, THEIR PREPARATION AND THEIR USE

[75] Inventors: Heinz Uhrig, Steinbach/Taunus; Erich Ackermann, Kelkheim; Reinhold Deubel, Bad Soden am Taunus, all of Fed. Rep. of Germany

[73] Assignee: Hoechst Aktiengesellschaft, Frankfurt am Main, Fed. Rep. of Germany

[21] Appl. No.: 239,509

[22] Filed: Sep. 1, 1988

[30] Foreign Application Priority Data

Sep. 4, 1987 [DE] Fed. Rep. of Germany ....... 3729657

[51] Int. Cl.$^5$ .................... C08G 8/34; C09F 1/04
[52] U.S. Cl. .................... 527/602; 527/603; 530/215; 530/218
[58] Field of Search ............. 530/215, 218; 527/602, 527/603

[56] References Cited

U.S. PATENT DOCUMENTS

| | | | |
|---|---|---|---|
| 2,478,490 | 8/1946 | Krumbhaar | 527/602 |
| 2,736,664 | 2/1956 | Bradley et al. | 530/218 |
| 2,950,313 | 8/1960 | Kirkpatrick | 530/218 |
| 3,306,901 | 2/1967 | Ohnacker . | |
| 3,775,056 | 11/1973 | Grossmann et al. | 8/169 |
| 3,998,652 | 12/1976 | Aign et al. | 106/300 |
| 4,009,142 | 2/1977 | Deubel et al. . | |
| 4,297,270 | 10/1981 | Uhrig et al. | 530/215 |
| 4,312,631 | 1/1982 | Luntze et al. | 530/218 |
| 4,391,640 | 7/1983 | Okoshi et al. | 527/602 |
| 4,403,079 | 9/1983 | Uhrig et al. | 525/507 |
| 4,539,128 | 9/1985 | Grossmann et al. | 252/49.3 |
| 4,703,077 | 10/1987 | Webb | 524/487 |
| 4,775,496 | 10/1988 | Wideman et al. | 530/218 |

FOREIGN PATENT DOCUMENTS

| | | |
|---|---|---|
| 0058384 | 8/1982 | European Pat. Off. . |
| 0065751 | 12/1982 | European Pat. Off. . |
| 0071167 | 2/1983 | European Pat. Off. . |
| 0305885 | 3/1989 | Fed. Rep. of Germany ....... 527/602 |
| 1264014 | 11/1986 | Japan .................... 527/603 |

OTHER PUBLICATIONS von Hofmann, H. M. R., "Die En-Reaktion", *Agnew. Chem. 81*, 597-618 (1969).

*Primary Examiner*—John Kight, III
*Assistant Examiner*—Rabon Sergent

[57] ABSTRACT

The invention relates to surface-active compounds of the general formula (I)

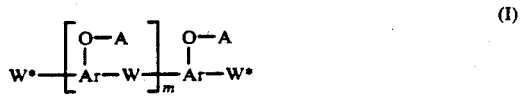

in which Ar is an aromatic system which is optionally substituted by $C_1$-$C_{18}$-alkyl, $C_1$-$C_{18}$-alkoxy, $C_2$-$C_5$-alkanoyl, $C_6$-$C_{10}$-aryl, ($C_6$-$C_{10}$-aryl)-$C_1$-$C_4$-alkyl, A has the formula $-(X-O)_n-Y$, wherein n denotes 1 to 50, X denotes ethylene or methylethylene and all or some of Y denote an acyl radical of a non-modified or modified natural resin acid and the other radicals Y denote radicals from the group comprising hydrogen, acyl radicals of saturated $C_{1-24}$-carboxylic acids, unsaturated $C_{3-24}$-carboxylic acids, $C_{2-24}$-hydroxy-fatty acids or $C_{8-18}$-alkyl-, -alkenyl- and -alkylidene-succinic acids, maleic acid, fumaric acid, sulfosuccinic acid, sulfuric acid, benzodicarboxylic acids and $C_{2-16}$-n-alkanedicarboxylic acids, W is a group $-CHR-$ or $-CHR-N(R^*)-T-N(R^*)-CHR-$, wherein $R^*$ is hydrogen, $C_1$-$C_4$-alkyl, $C_2$-$C_4$-hydroxyalkyl, a radical A or $-C_2$-$C_4$-alkylene-O-A and R is H or $C_{1-9}$-alkyl, T is $C_2$-$C_{12}$-alkylene, which is optionally interrupted by $-O-$ or $-NR'-$, $R'$ is H, $C_1$-$C_4$-alkyl, $C_2$-$C_4$-hydroxyalkyl, A or $C_2$-$C_4$-alkylene-O-A, W* is H or $-CHR-N(R^*)-T-N(R^*)A$ and m is 1 to 16.

The compounds are prepared on the basis of oxyalkylated novolaks of the formula (I) in which all the radicals Y denote hydrogen. The polyalkylene glycol chains are now terminally esterified or half-esterified in a one- or multi-stage reaction in accordance with the definition of A. The resulting surface-active products are suitable as emulsifiers and dispersing agents for the most diverse fields of applications.

5 Claims, No Drawings

RESIN ACID ESTERS BASED ON NOVOLAK OXYALKYLATES, THEIR PREPARATION AND THEIR USE

The invention relates to the technical field of surface-active agents which can be used, in particular, as auxiliaries in the preparation of solids dispersions and emulsions and as coupling auxiliaries in the preparation of azo coloring agents or as dyeing auxiliaries.

A large number of nonionic, anionic and also cationic surfactants are used in the preparation of dispersions of coloring agents such as pigments or disperse dyestuffs. The nature of the surfactants has a substantial influence on the fine distribution and therefore the tinctorial strength of the coloring agents in the particular use media. The viscosity, gloss and storage stability are also influenced decisively by the nature of the surfactants. Surfactants are also usually employed in the preparation of azo dyestuffs from sparingly soluble coupling component, and they facilitate good distribution of the coupling component in the reaction medium and a complete reaction during azo coupling.

Anionic alkylphenol-novolak oxyalkylate esters which contain sulfosuccinic acid half-ester groups as anionic groups are known as dispersing agents from DE-A-2,132,403 (U.S. Pat. No. 3,775,056) and DE-A-2,132,404 (U.S. Pat. No,. 4,009,142).

Nonionic water-soluble dispersing agents which are prepared by condensation of aromatic compounds containing phenolic hydroxyl groups with formaldehyde and amines and subsequent oxyalkylation are described in DE-A-2,421,606 (U.S. Pat. No. 3,998,652). Mixed esters of oxyalkylated alkylphenol-and alkylnaphthol-novolaks in which phthalic acid, benzoic acid, naphthoic acid, maleic acid and sulfosuccinic acid occur as acid components are moveover known as dispersing agents and coupling auxiliaries from EP-A-0,058,384 (U.S. Pat. No. 4,403,079) and EP-A-0,065,751 (U.S. Pat. No. 4,403,077). Coolants and lubricants for metal cutting are moreover described in EP-A-0,071,167 (U.S. Pat. No. 4,539,128). The auxiliaries can be obtained by esterification of oxyalkylated phenol- and nonylphenol-novolaks with fatty acids.

The compounds of the prior art mentioned are low-foaming, anionic surface-active agents and are suitable as dispersing agents in the preparation of coloring agent dispersions and as wetting, emulsifying, leveling ad dyeing auxiliaries and also as coolants in metalworking.

The present invention also relates to structurally modified compounds which impart considerably improved surface-active properties.

The invention relates to water-soluble compounds of the general formula (I)

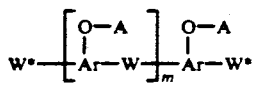

(I)

in which the radical Ar, in each case independently of the other radicals Ar, is a radical of an aromatic system, preferably a benzene, naphthalene or biphenyl radical, which is in each case not further substituted or substituted by one or more radicals from the group comprising saturated or unsaturated $C_1$-$C_{18}$-alkyl, $C_1$-$C_{18}$-alkoxy, $C_2$-$C_5$-alkanoyl, $C_6$-$C_{10}$-aryl and ($C_6$-$C_{10}$-aryl)-$C_1$-$C_4$-alkyl, preferably an aryl radical which is not further substituted or an aryl radical which is substituted by $C_1$-$C_{12}$-alkyl, in particular $C_1$-$C_9$-alkyl, or by acetyl, the radical A in each case independently of the other radicals A denotes a group of the formula —(X—O)$_n$—Y, in which n is an integer from 1 to 150, preferably from 1 to 50 and in particular from 5 to 25, the radical X in each case independently of the other radicals X denotes a group of the formula —$CH_2CH_2$—, —$CH_2CH(CH_3)$— or —$CH(CH_3)CH_2$— and all the radicals Y or some of the radicals Y, preferably one another, represent an acyl radical of a non-modified or modified natural resin acid and the other radicals Y preferably 90–50% of the radicals Y, in each case independently of one another represent a radical or various radicals from the group comprising hydrogen, an acyl radical of a saturated carboxylic acid with 1–24 carbon atoms of an unsaturated carboxylic acid with 3–24 carbon atoms, preferably of a saturated or unsaturated fatty acid with 8–18 carbon atoms, of a hydroxycarboxylic acid with 2–24 carbon atoms, preferably of a hydroxy-fatty acid with 8–18 carbon atoms, or of an alkyl-, alkenyl- or alkylidenesuccinic acid with in each case 8–18 carbon atoms in the side chain, and acyl radicals of the formulae —CO—CH=CH—COOM, —COCH$_2$CH(SO$_3$M)—COOM, —CO—(CH$_2$)$_p$—COOM, —CO—C$_6$H$_4$—COOM and —SO$_3$M, wherein, in the above formulae, p is a number from 0 to 14, preferably 2 to 6, and M stands for the equivalent of a cation, preferably an alkali metal cation, one equivalent of an alkaline earth metal cation, ammonium, a substituted ammonium group with 1–4 $C_1$-$C_4$alkyl or $C_1$-$C_4$-hydroxyalkyl groups or an ammonium group which is obtained by addition of up to 150 mol equivalents of ethylene oxide or propylene oxide (or both) onto ammonia or onto a mono-, di- or trialkylamine with 1–4 carbon atoms in the alkyl radical, the radical W, in each case independently of one another, denotes a divalent group of the formula —CHR— or —CHR—N(R*)—T—N(R*)—CHR— wherein, in the above formulae, the radical R*, independently of one another, represents hydrogen, $C_1$-$C_4$-alkyl, $C_2$-$C_4$-hydroxyalkyl, a radical of the formula A or —Q—O—A, preferably A, and A having one of the meanings given above, and Q is a $C_2$-$C_4$-alkylene group, the radical R, in each case independently of one another, represents hydrogen or $C_1$-$C_9$-alkyl, in particular hydrogen or $C_1$-$C_4$-alkyl, and the radical T, in each case independently of one another, represents $C_2$-$C_{12}$-alkylene, preferably $C_2$-$C_6$-alkylene or $C_2$-$C_{12}$-alkylene, which is interrupted by at least one of the divalent groups —O— and —NR'—, which do not stand side by side and wherein R' is hydrogen, $C_1$-$C_4$-alkyl, $C_2$-$C_4$-hydroxyalkyl, A or —Q—O—A, and A and Q having one of the meanings given above, the radical W*, in each case independently of one another, denotes hydrogen or a group of the formula —CHR—N(R*)—T—N(R*)A, in which R, R*, A and T have the meanings given, and m denotes an integer from 1 to 16, preferably 3 to 8.

Compounds of the formula (I) according to the invention in which some of the radicals Y consist of the anionic radicals mentioned, in particular anionic radicals of the formula —CO—CH=CH—COOM or —CO—CH$_2$CH(SO$_3$M)—COOM or both, preferably of the radicals of the formula —COCH$_2$—CH(SO$_3$M-

)—COOM, M in the formulae having the abovementioned meaning, are of particular interest.

Independently of this, compounds of the formula (I) according to the invention in which W stands for a group of the formula —CHR—, in which R has the meaning given, and preferably denotes hydrogen, X stands for the group of the formula —$CH_2CH_2$—, W* stands for hydrogen or a group of the formula —CHR—NA—T—$NA_2$, in which R, T and A have the meanings given, n stands for a number from 1 to 50, preferably 5 to 25, and m stands for a number from 3 to 8, are of particular interest.

Compounds of the formula (I) in which Ar is a benzene or naphthalene radical, each of which is not further substituted or is substituted by one or more, preferably not more than one $C_1$-$C_9$-alkyl radical or one acetyl radical, some of the radicals Y, in particular 20 to 40% of the radicals Y, in the radicals A in each case denote an acyl radical of a non-modified or a modified natural resin acid, if appropriate some of the radials Y, in particular 0 to 40% of the radicals Y, in each case denote an acyl radical of a saturated or unsaturated fatty acid with 8—18 carbon atoms or of an alkyl-, alkenyl- or alkylidenesuccinic acid with 8-18 carbon atoms in the side chain or if appropriate hydrogen or a mixture thereof, and the remaining radicals Y, in particular 80 to 20% of the radicals Y, in each case denote a half-ester group of maleic acid, sulfosuccinic acid, phthalic acid or sulfuric acid, in particular an acyl radical of the formula —CO—CH=CH—COOM or of the formula —$COCH_2CH(SO_3M)$—COOM, the percentages of the radicals summing up to 100% wherein, in the formulae, M has the meaning given, W preferably denotes a divalent group of the formula —CHR—, in which R denotes hydrogen or $C_1$-$C_4$-alkyl, W* preferably in each case denotes hydrogen and m preferably denotes an integer from 3 to 8, are preferred.

The invention also relates to the process for the preparation of the compounds of the formula (I) according to the invention, which comprises esterifying compounds of the formula (I) in which Ar, W, W*, A, X, m and n have the abovementioned meanings, but Y in each case denotes hydrogen, on all or some of the terminal hydroxyl groups with non-modified or modified natural resin acids and leaving the remaining terminal hydroxyl groups non-modified or at least partly converting them into the corresponding ester or half-ester groups in a one- or multistage reaction with at least one compound or a combination of compounds from the group comprising: saturated or unsaturated carboxylic acids with 1-24 carbon atoms, preferably fatty acids with 8-18 carbon atoms, hydroxycarboxylic acids with 2-24 carbon atoms, preferably hydroxy-fatty acids with 8-18 carbon atoms, alkyl-, alkenyl- and alkylidene-succinic acids with 8-18 carbon atoms in the side chain, acids of the formulae HOOC—CH=CH—COOH, HOOC—$(CH_2)_p$—COOH, HOOC—$C_6H_4$—COOH, $H_2SO_4$ and $ClSO_3H$, wherein p has the meaning given, and anhydrides of the compounds of the abovementioned formulae, preferably $SO_3$ or maleic anhydride, with subsequent reaction with a sulfite, and leaving the resulting compounds in the acid form or, preferably, converting them into the corresponding salt form by replacing the acid hydrogen atoms by one equivalent of a cation, preferably an alkali metal cation, one equivalent of an alkaline earth metal cation, ammonium, a substituted ammonium group with 1 to 4 $C_1$-$C_4$-alkyl or $C_1$-$C_4$-hydroxyalkyl groups or an ammonium group which is obtained by addition of up to 150 ml equivalents of ethylene oxide or propylene oxide (or both) onto ammonia or onto a mono-, di- or trialkylamine with 1–4 carbon atoms in the particular alkyl radical.

The oxyalkylated novolaks of the formula (I), in which Y denotes hydrogen, used for the process according to the invention can be obtained by processes which are customary per se, for example by processes analogous to those described in German Offenlegungsschriften Nos. 2,132,403, 2,132,404 and 2,421,606 and in European Patent Application publications EP-A-58,384, -65,751 and -71,167 for the preparation of oxyalkylated novolaks.

The abovementioned novolaks in which W denotes a divalent group of the formula —CHR— can thus be prepared by condensation of about (m+1) mol equivalents of one or more aromatic hydroxy compounds of the formula Ar—OH with m mol equivalents of aldehydes of the formula RCHO and subsequent oxyalkylation. Preferably, a molar ratio of aromatic:aldehyde of 3:2 to 17:16, in particular 4:3 to 9:8, is used and the condensation is carried out in the presence of acid catalysts.

Analogous starting substances in which at least one radical W* is a radical of the formula —CHR—N(R*)—T—N(R*)A can be prepared analogously to the abovementioned starting substances but by carrying out, before the oxyalkylation, a condensation with a mixture of aldehyde RCHO and amine of the formula (R*)NH—T—NH(R*), wherein R* and T can have the meanings given, but as a rule do not contain the radical A or —Q—O—A, and at the same time using the amine in the mixture in a molar ratio of 1:1 or in a molar excess with respect to the aldehyde RCHO.

Oxyalkylated novolaks of the formula (I) in which Y denotes hydrogen and at least one radical W denotes a group of the formula —CHR—N(R*)—T—N(R*)—CHR— can be obtained by condensation of the aromatic hydroxy compounds Ar—OH mentioned with a mixture of the aldehyde RCHO mentioned and amine (R*)NH—T—N(R*)H mentioned in a one-stage or multi-stage procedure with subsequent oxyalkylation. The amount of aldehyde in the one-stage reaction is preferably at least about one mole equivalent per reactive amino group of the amine, that is to say in the case of diamines of the formula mentioned at least about twice the molar amount of aldehyde per mole of diamine. The molar ratio of the aromatic hydroxy compound Ar—OH to the sum of the molar amount of diamine and the molar amount of aldehyde, possibly in excess, which exceeds twice the molar amount of diamine, should be chosen at about (m+1):m, (m+1) denoting the number of nuclei of the novolak.

In the multi-stage procedure, the first stage can preferably be carried out as described above, and the reaction with another aldehyde or aldehyde-amine mixture is carried out in the second process stage. Preferably, end groups W* of the formula —CHR—N(R*)—T—N(R*)A, in which A is initially hydrogen and after further modification, such as oxyalkylation and esterification, can have the meanings given, can be obtained with a second process stage by condensation with a mixture of aldehyde RCHO and amine of the formula (R*)NH—T—N(R*)H, the amine being used in a molar ratio of 1:1 or in excess with respect to the aldehyde.

The molar ratios stated do not have to be observed exactly. Mixtures of novolaks with a different number of aromatic nuclei per molecule are in any case usually formed during novolak formation, so that as a rule only the number of nuclei of the main products can be stated, from the proportions of the starting substances.

Aromatic hydroxy compounds Ar—OH are to be understood here as aromatic compounds in which a hydroxyl group is bonded to an aromatic nucleus and thus has phenolic character. In addition, the aromatic hydroxy compounds must have at least two positions on the aromatic system which are reactive in the sense of novolak formation. Examples of such aromatic hydroxy compounds are phenols, such as hydroxybenzene, 1-naphthol, 2-naphthol, tetrahydronaphthols, arylated phenols, in particular 4-phenylphenol and 2-, 3- and 4-methoxyphenol and -ethoxyphenol, C-acylated phenols, such as 2-, 3- and 4-acetylphenol and 2- and 4-propionylphenol, alkylphenols, such as 2-, 3-and 4-monoalkylphenols with straight-chain or branched $C_1$-$C_{18}$-alkyl radicals, in particular o-, m- and p-cresol and o-, m- and p-ethyl-, -propyl-, -isopropyl-, -butyl-, -isobutyl-, -2-butyl-, -t-butyl-, -pentyl-, -isopentyl-, -neopentyl-, -hexyl-, -heptyl-, -octyl-, -nonyl-, -decyl-, -undecyl-, -dodecyl-, -tridecyl-, -tetradecyl-, -pentadecyl-, -hexadecyl-, -heptadecyl- and -octadecylphenol-, preferably with straight-chain alkyl radicals, in particular with $C_1$-$C_9$-alkyl radicals, corresponding alkylnaphthols, in particular oxtyl- and nonylnaphthol, dialkylphenols, such as xylenols and dibutyl-, dioctyl-, -dinonyl- and ditetradecylphenol, and dialkylnaphthols, such as dibutyl-, dioctyl-, dinonyl-and ditetradecylnaphthols. Compounds of the formula (I), in which Ar stands for an arylalkyl-substituted aromatic compound, can also be prepared by arylalkylation of the not yet oxyalkylated novolaks with arylalkenes—for example with vinylbenzene in the presence of acid catalysts.

As examples of the aldehydes which can be used in the condensation, the following may be mentioned: formaldehyde, in particular used as formaldehyde-liberating compounds such as paraformaldehyde, trioxane, tetraoxymethylene, formaldehyde dimethyl acetal and hexamethylenetetraamine, and acetaldehyde or paraldehyde, propionaldehyde, butyraldehyde, valeraldehyde, capronaldehyde, heptanal, octanal and nonanal, preferably formaldehyde and formaldehyde equivalents such a paraformaldehyde.

Examples of the amines of the formula HN(R°)—T—N(R°)H are diamines, such as 1,2-diaminoethane, 1,3-diaminopropane, 1,4-diaminobutane, 1,5-diaminopentane, 1,6-diaminohexane, N,N'-dimethylethylenediamine, N-(2-hydroxyethyl)-ethylenediamine, N-methylpropylenediamine, N,N'-dimethylpropylenediamine, N-butylpropylenediamine, N-butylpropylenediamine, 1,8-diaminooctane, 1,6-diamino-2,2,4-trimethyl-hexane, bis-(3-aminopropyl) ether, bis-(3-aminopropyl)-methylamine and preferably diamines with primary amino groups, in particular 1,2-diaminoethane, 1,3-diamino-propane, 1,4-diaminobutane, 1,5-diaminopentane and 1,6-diaminohexane.

The following acids are suitable, for example, as acid catalysts in the reaction of aldehydes or aldehydes and amines with the aromatic hydroxy compounds: oxalic acid, formic acid, mineral acids, such as sulfuric acid, phosphoric acid and preferably hydrochloric acid, and sulfonic acids, such as dodecylbenzenesulfonic acid. Hydrochloric acid is preferred, because it can easily be removed during removal of water. The acid catalysts are preferably used in a concentration of 0.1-5% by weight. The condensation is carried out at a temperature of 20°-150° C., preferably at 80°-130° C., as a rule under a nitrogen atmosphere. After the condensation, the water is advantageously distilled off under reduced pressure, a water content in the resin of less than 0.3% being achieved towards the end under a reduced pressure of less than 66 mbar.

The oxylakylation of the novolak resins is carried out by known methods, preferably with alkali metal hydroxides or alkoxides as the catalyst, at 100°-200° C., in particular at 1340°-180° C. The amount of ethylene oxide or propylene oxide or both is chosen so that a stable emulsifiability or complete solubility of the addition products in water is preferably achieved. In each case 1 to 150, preferably 1-50 and in particular 5-25 molecules of ethylene oxide or propylene oxide or both are advantageously added onto each hydroxyl group of the novolak resins and to each hydrogen atom of the secondary and primary amino groups present. The amount of alkylene oxide added on its also chosen according to the intended use and thus the degree of hydrophilicity sought. Potassium hydroxide or preferably sodium hydroxide is suitable as the alkali metal hydroxy and sodium methylate or ethylate is suitable as the alkali metal alkoxide; the concentration of the alkaline catalysts should preferably be 0.05-2.0% by weight, based on the novolak resin, at the start of the oxyalkylation. The oxyalkylation can be carried to under normal pressure or in pressure vessels with propylene oxide or preferably with ethylene oxide or mixtures of the two, it being possible for the alkylene oxide to be fed in as a gas or liquid. The operating pressure is a rule 1-10, preferably 2-4 bar.

The esterification of the oxyalkylated novolaks is carried out in one of more reaction stages. It is thus possible to react in the first reaction stage all or some of the hydroxyl groups, but at least one hydroxyl group, of the oxyalkylated novolak with a non-modified or modified natural resin acid or a reactive derivative thereof, preferably with resin acids such as abietic acid, dehydroabietic acid, tetrahydroabietic acid, levopimaric acid, dextropimaric acid and isodextropimaric acid, such as are present in commercially available grades of colophony, and modified resin acids, such as disproportionated, hydrogenated and dimerized natural resin acids.

Modified natural resin acids as are obtained by reaction of natural resin acids with araliphatic or aromatic compounds which split off halogen, such as benzyl chloride, o-, m- and p-bis-(chloromethyl)-benzene, 2-, 3-, and 4-chloromethyl-toluene, benzal chloride, 1-and 2-chloromethylnaphthalene, 2-, 3- and 4-chlorophenol, 5-chloro-2-hydroxytoluene, 2-chloro-5-hydroxy-1,3-xylene, 4-chlorodiphenyl, 1- and 2-chloronaphthalene, 1-chloro-2-naphthol and 2-chloro-1-naphtol, or with cycloaliphatic compounds, such as cyclohexyl chloride, in the presence of a catalyst, such as zinc chloride, at a temperature of 100°-220° C., 0.5-1 mole of the chlorohydrocarbons mentioned being used per mole of resin acid, are also suitable for the esterification.

Resin-phenol compounds, such as are obtained by addition of phenols, such as hydroxybenzne, o-, m- and p-cresol, orthocresol acetate, salicylic acid, guaiacol, bisphenol A, α-naphthol and β-naphthol onto naturally occurring resin acids or commercially available grades of colophony, in the presence of strongly acid catalysts or catalysts which split off an acid, such as, for example, boron trifluoride, hydrogen chloride, tin tetrachloride, aluminum trichloride or mineral acids, at a temperature of preferably 20° to 120° C. in an organic medium, or in the presence of a strongly acid ion exchanger at preferably 120° to 200° C., in particular at 150° to 170° C., 0.05 to 0.8, preferably 0.65 to 0.75 mole of the phenols mentioned being used per mole of resin acid, are moreover suitable as modified natural resin acids for the esterification.

The natural resin acids or modified natural resin acids are esterified with the oxyalkylated novolaks by esterification methods which are customary per se. The reaction temperature as a result is between room temperature and 240° C., depending on the esterification method. The esterification is preferably carried out in an inert organic solvent which is suitable as an entraining agent for removing the water of reaction in order to increase the yield. The esterification is preferably carried out in xylene as the organic solvent and in the presence of acid catalysts at a temperature of 130°-220° C. Acids and Lewis acids, such as benzenesulfonic acid, p-toluenesulfonic acid, boric acid, tin powder, zinc chloride and sulfuric acid, can be used as the acid catalysts.

The nonionic resin acid esters obtained in the first reaction stage are useful surface-active agents as such and can be used in the context of the invention. Alternatively, the nonionic resin acid esters obtained can be esterified on the remaining hydroxyl groups or some of the hydroxyl groups in a second reaction stage with saturated or unsaturated carboxylic acids or hydroxycarboxylic acids, in particular fatty acids or hydroxy-fatty acids, such as, for example, acetic acid, propionic acid, butyric acid, valeric acid, caproic acid, heptanoic acid, octanoic acid, pelargonic acid, capric acid, lauric acid, myristic acid, palmitic acid, steric acid, arachic acid, behenic acid, oleic acid, linoleic acid, tallow fatty acid and ricinoleic acid, preferably the fatty acids mentioned with 12-18 carbon atoms, in particular those such as are in the form of commercially available fatty acids or fatty acid mixtures. The esterification with the carboxylic acids or fatty acids mentioned can be carried out analogously to the esterification with the modified or non-modified natural resin acids. It is also possible for the esterification with the fatty acids to be carried out before or at the same time as the esterification with the resin acids.

Alternatively, free hydroxy groups can be half-esterified with alkyl-, alkenyl- or alkylidenesuccinic acid or -succinic anhydrides in he second reaction stage or in a third reaction stage. Suitable α-alkylated succinic acids are, in particular, those with straight-chain radicals from the group comprising octyl, nonyl, decyl, undecyl, dodecyl, tridecyl, tetradecyl, pentadecyl, hexadecyl, heptadecyl and octadecyl, which preferably have a double bond, in particular a double bond between the second and third carbon atoms in the alkyl radical, and α-alkylated succinic acids or anhydrides in which a branched saturated or unsaturated $C_8$-$C_{12}$-alkyl radical, in particular tripropylene or tetrapropylene radical, is present. Preferred α-alkylated succinic acids are obtainable, for example, by reaction of n-octene, n-nonene, n-decene, n-undecene, n-dodecene, n-tridecene, n-tetradecene, n-pentadecene, n-heptadecene, n-hexadecene, n-heptadecene, n-octadecene, tripropylene or tetrapropylene with maleic anhydride in the presence of acid catalysts (see, for example, Angew. Chem. 81, pages 597-618 (1969), "Ene reaction" and the literature quoted there, as well as U.S. Pat. No. 3,306,901).

The esterification with α-alkylated succinic anhydrides is preferably carried out at 20°-100° C., in particular 40°-80° C., in the presence of 0.1-1.0% by weight of alkali metal hydroxides, based on the total mixture.

The esterification of the oxyalkylated novolaks with the resin acids mentioned so far or resin acids in combination with carboxylic acids with alkyl radicals, preferably with long alkyl radicals, can alternatively also be carried out by transesterification using the corresponding alkyl esters, preferably methyl esters, of the resin acids or carboxylic acids mentioned in the presence of 0.1-1.0 mol equivalents of alcoholate, preferably sodium methylate, at 150°-200° C., preferably 160°-190° C., the alkanol or methanol liberated being distilled off.

The resin acid esters and mixed esters with resin acids and carboxylic acids of the oxyalkylated novolaks which have been mentioned so far are preferably reacted with dicarboxylic acids, sulfuric acid or chlorosulfonic acid or corresponding anhydrides in a further reaction stage, so that anionic ester groups are introduced. Examples of suitable dicarboxylic acids or anhydrides thereof for the esterification are: maleic acid, maleic anhydride, fumaric acid, phthalic acid, phthalic anhydride, isophthalic acid, terephthalic acid, oxalic acid, malonic acid, succinic acid, succinic anhydride, glutaric acid, adipic acid, pimelic acid, suberic acid, azelaic acid and sebacic acid. The anionic groups are preferably converted by reaction of maleic anhydride or phthalic anhydride by mixing and stirring at 20°-100° C., preferably at 40°-80° C., in the presence of alkali metal hydroxides. The concentration of the alkali metal hydroxides should be 0.1-1.0% by weight, based on the total mixture. In the case of maleic anhydride, because of the tendency towards sublimation it is advantageous to carry out the reaction in pressure vessels under an increased pressure of 0.2-1.0 bar of nitrogen or air and to ensure vigorous thorough mixing, since the molten maleic anhydride is poorly miscible with the partly esterified oxyalkylates at the start of the reaction.

In the case of maleic acid half-ester groups which have been introduced, it is also advantageous to convert the half-ester groups into the corresponding sulfosuccinic half-ester groups. This is effected, for example, after addition of aqueous solutions of sulfites or bisulfites to the compounds containing maleic acid half-ester groups. 1.0-1.5, preferably 1.0-1.1 mole of sulfurous acid in the form of alkali metal or alkaline earth metal sulfites, bisulfites or pyrosulfites are preferably used per maleic acid half-ester group. The amount of water added is as a rule about 50-85% by weight, based on the total solution or mixture, and depends on the solubility of the sulfosuccinic acid half-ester salts and the viscosity of the solutions. The reaction temperature in the reaction of sulfites with the maleic acid half-ester compounds is as a rule 20°-100° C., preferably 40°-80° C.

Whilst sulfites are particularly suitable for the formation of the di-alkali metal salts of the sulfosuccinic acid half-esters, where bisulfites are added on it is possible additionally to influence the degree of hydrophilicity by neutralization with bases, such as ammonia, low molecule alkylamines or alkylolamines or alkylene oxide adducts thereof, up to about 150 moles of ethylene oxide or propylene oxide or both being adding on per mole of amine or alkylolamine and up to 150, preferably 5-30 mol equivalents of ethylene oxide or propylene oxide or both being adding on per reactive hydrogen atom in the compounds mentioned. Representatives of the alkylamines or alkylolamines which may be mentioned are: ethylamine, propylamine, isopropylamine, butylamine, isobutylamine, monoethanolamine, monopropanolamine, monoisopropanolamine, monobutanolamine, monoisobutanolamine, diethanolamine, dipropanolamine, or tributanolamine and di- and polyamines, such as ethylenediamine, ethylenetriamine, triethylenetetramine, propylenediamine, dipropylenediamine, dipropylenetriamine or tripropylenetetramine.

The cation exchange described by the example of the sulfosuccinic acid half-esters can also be carried out on the compounds of the formula (I) which contain other anionic groups. The compounds are thereby used in their acid form and are converted into the corresponding salts in an analogous manner by neutralization with the abovementioned amines or inorganic bases. Other customary cation exchange processes can also be used.

The sulfation of free hydroxyl groups of the oxyalkylated and partly esterified novolaks can be carried out by known processes, it being possible to use, for example, sulfuric acid, chlorosulfonic acid, amidosulfonic acid, $SO_3$ gas diluted with inert gas or an $SO_3$ adduct, for example $SO_3$-dioxane, as the sulfating reagent. The sulfation is carried out with good thorough mixing, if necessary with the addition of an inert diluent, for example methylene chloride. Temperatures of 0° to about 150° C. are thereby maintained, depending on the sulfating agent. The amount of sulfating reagent to be used can be chosen so that all the free hydroxyl groups or only some of them are still reacted.

Whilst the ammonium salts of the sulfuric acid half-esters are obtained on sulfation with amidosulfonic acid, the embodiment which is of the most industrial interest using gaseous sulfur trioxide mixed with an inert gas and also sulfation with chlorosulfonic acid gives the sulfuric acid half-esters in the acid form, from which the desired salts can easily be prepared by neutralization with corresponding inorganic or organic bases. The alkali metal hydroxides, which lead to the very readily water-soluble alkali metal salts of the sulfuric acid half-esters according to the invention, are preferably used for this neutralization.

The invention also relates to the use of the compounds of the formula (I) according to the invention as surface-active agents. The compounds according to the invention or their mixtures are substances which, because of their favorable surface-active properties, have extremely varied uses. Thus, they give stable emulsions in water or are clearly soluble in water. They lower the surface tension measured by the ring pull-off method (DIN 53914) and are low-foaming to almost foam-free in accordance with the Ross-Miles test (DIN 53902). They moreover wet cotton fabric by the immersion wetting method (DIN 53901) and are stable towards alkali and strong acids under the customary conditions of use of surfactants. The substances according to the invention can be used either as emulsifiers or as dispersing agents for the most diverse fields of application. This applies above all to use as coupling auxiliaries or preparation agents or both in the manufacture of azo compounds, in particular azo pigments. They are moveover suitable as dispersing agent sin the preparation of coloring agent dispersions, preferably disperse dyestuffs, and furthermore for formulating pigment preparations, plant protection agents and agents for combating pests and carrier emulsions, and as leveling and dyeing auxiliaries. The products are biologically degradable.

The compounds according to the invention can be used individually or as mixtures or in combinations with other nonionic, anionic or cationic surfactants or mixtures thereof. They can moreover be used together with builders substances or other customary additives or auxiliaries.

In the following examples, "parts" relate to the weight, and parts by volume bear the same relationship to parts by weight as the kilogram to the liter. Pressure data denote "increased pressure", based on atmospheric pressure, unless indicated otherwise.

1. PREPARATION OF THE NOVOLAKS (1.1) 7-Nucleus nonylphenols-novolak: 1,540 parts of nonylphenol, 189.5 parts of paraformaldehyde and 10.9 parts of 4-dodecylbenzenesulfonic acid are mixed at room temperature and the mixture is stirred under reflux under a nitrogen atmosphere for 14 hours. The internal temperature is then increased to 135° C. and the water of reaction is distilled off in the course of 4 hours. The mixture is then subsequently stirred at 135°-140° C. under a reduced pressure of about 20-30 mbar for two hours. 1,606 parts of a pale yellow brittle resin are obtained.

(1.2) 9-Nucleus nonylphenol-novolak: 1,980 parts of nonylphenol, 252.7 parts of paraformaldehyde and 13.9 parts of 4-dodecylbenzenesulfonic acid are stirred under reflux for 15 hours analogously to compound 1.1 and the mixture is worked up as described there. 2,077 parts of resin are obtained.

(1.3) 7-Nucleus p-cresol-novolak: 728 parts of p-cresol are stirred under reflux with 189.5 parts of paraformaldehyde and 4.3 parts of concentrated hydrochloric acid for 15 hours analogously to Example 1.1 and the mixture is worked up as described there. 750 parts of novolak resin are obtained.

(1.4) 4-Nucleus novolak: 440 parts of nonylphenol and 174 parts of hexamethylenediamine are stirred and mixed at an internal temperature of 50°-60° C. for 3 hours, under the cover of a nitrogen atmosphere. 90 parts of paraformaldehyde are then added in portions in the course of 3 hours and the mixture is stirred thoroughly. After dropwise addition of a solution of 1.5 parts of dodecylbenzenesulfonic acid and 9 parts of water and after an after-stirring time of 60 minutes, the internal temperature is increased to 90° C. and condensation is carried out for 5 hours, the water of reaction being distilled off. The pressure if then reduced to 20-30 mbar and the mixture is subsequently stirred at 9°-100° C. for 3 hours. 600 parts of a pale red-brown solid novolak resin are obtained as the yield.

1.5) 5-Nucleus nonylnaphthol-novolak: 1,350 parts of nonyl-$\beta$-naphthol are taken and 132 parts of paraformaldehyde are introduced at room temperature, while stirring slowly. The mixture is stirred at 50° C. for one hour, under a cover of nitrogen gas, the internal temperature is increased to 90° C. and 15.1 parts of concentrated hydrochloric acid are added dropwise. The mixture is then stirred at 110° C. for 10 hours, while simultaneously passing through nitrogen gas, the internal temperature is increased to 135°-140° C. and the water of reaction is largely removed in the course of 4 hours. After the pressure has been reduced to about 20-30 mbar, the mixture is subsequently stirred at 135°-140° C. for a further 2 hours. After cooling, 1,330 parts of dark-colored, red-brown solid resin are obtained.

(1.6) 5-Nucleus p-phenylphenol-novolak: 425 parts of a p-phenylphenol are taken and 60 parts of paraformaldehyde are introduced in portions at an internal temperature of 60°-75° C. in the course of 2 hours, while stirring slowly. The mixture is stirred at 75° C. for one hour, under a nitrogen gas atmosphere, the internal temperature is increased to 120° C. and a solution of 22.2 parts of dodecylbenzenesulfonic acid in 7 parts of water is added dropwise. The mixture is then stirred at 120°-130° C. for 10 hours, while passing through nitrogen gas, the water of reaction being largely removed. After the pressure has been reduced to about 20-30 mbar, the mixture is stirred at 120°-130° C. for a further 2 hours. After cooling, a brittle, green-brown solid novolak resin is obtained.

Yield: about 410 parts of novolak.

(1.7) Styrenized 7-nucleus phenol-novolak: 95.5 parts of paraformaldehyde are slowly added to 349 parts of phenol at an internal temperature of 50°-75° C. in the course of 2 hours, while stirring. After the mixture has been stirred for a further hour, the internal temperature is increased to 120°-125° C. and a solution of 2 g of dodecylenzenesulfonic acid in 10 ml of water is added dropwise in the course of 1.5 hours. The internal temperature is then increased t 130°-135° C. and the water of reaction and 22.5 parts of phenol are distilled off under reduced pressure over a period of 5 hours. The mixture is then stirred under a pressure of 20-30 mbar for a further 3 hours. After the internal temperature has fallen to 120°-125° C., 5 parts of oxalic acid are added and 339 parts of vinylbenzene are added dropwise in the course of 4-3 hours under a nitrogen gas atmosphere. After the mixture has been stirred at 130°-135° C. for a further 3 hours, 600 parts of a yellow-red solid novolak resin are obtained.

(1.8) 5-Nucleus novolak based on 4-hydroxyacetophenone: 200 parts of 4-hydroxyacetophenone are mixed thoroughly with a catalyst mixture of 1 part of oxalic acid and 0.5 part of dodecylbenzenesulfonic acid at an internal temperature of 90° to 100° C. and the mixture is subsequently stirred for a further hour under a layer of nitrogen gas. After the internal temperature has been increased to 100° C. to 110° C., 116.4 parts of a 36% strength aqueous formaldehyde solution are added dropwise in the course of 1 hour and after 2 hours the mixture is subsequently stirred at 100° C. to 110° C., while passing through nitrogen gas. After the internal temperature has been increased to 120° C. to 130° C., the water of reaction is largely removed in the course of 1 to 2 hours. After the pressure has been reduced to 20 to 30 mbar, the mixture is subsequently stirred at 130° to 135° C. for about a further hour. After cooling, 215 parts of pale-colored yellow-brown solid resin are obtained.

(1.9) 7-Nucleus 4-hydroxyacetophenone-novolak: 300 parts of 4-hydroxyacetophenone are stirred thoroughly with 1.5 parts of oxalic acid and 0.75 part of dodecylbenzenesulfonic acid at an internal temperature of 90° to 100° C. in the course of 1 hour, 13.3 parts of a 36% strength aqueous formaldehyde solution are added and the mixture is worked up analogously to Example (1.8). 320 parts of novolak resin are obtained.

2. PREPARATION OF THE NOVOLAK OXYALKYLATES (2.1) 1.2 parts of powdered caustic soda are added to 200 parts of novolak 1.1 and oxyalkylation is carried out, with stirring and introduction of 569 parts of ethylene oxide, a pressure of 2-4 bar and a temperature of 150°-160° C. being maintained. When all the ethylene oxide has been forced into the reaction vessel, the mixture is stirred at 150°-160° C. for a further hour. The resulting product is an oxyethylated 7-nucleus novolak with 105 oxyethylene units per molecule and with a hydroxyl number of 69. The hydroxyl number is a measure of the content of free hydroxy groups in the molecule; it corresponds to the amount of potassium hydroxide in mg which is needed to neutralize the amount of acetic acid consumed during esterification (acetylation) of 1 g of the test substance.

(2.2) 200 parts of 7-nucleus novolak 1.1 are oxyalkylated in a pressure vessel with the addition of 4.5 parts of sodium methylate, with stirring and with the introduction of 333 parts of propylene oxide and 524 parts of ethylene oxide at 145°-170° C., a pressure of about 3.4-5 bar being maintained. When all the alkylene oxide ha been forced into the pressure vessel, the mixture is stirred at 150°-160° C. for a further hour. The resulting resin oxyalkylate contains, as the main product, an oxyalkylated 7-nucleus nonylphenol-novolak with on average 48.3 oxypropylene units and 96.7 oxyethylene units per molecule. The product has a hydroxyl number of 45-46.

(2.5) After addition of 1.0 part of sodium hydroxide, 200 parts of novolak 1.2 are oxyethylated with 567.8 parts of ethylene oxide as described for Example 2.1. The resulting product chiefly corresponds to a 9-nucleus novolak oxyethylate with 135 oxyethylene units per molecule and a hydroxyl number of 63.

(2.4) After addition of 1.0 parts of powdered caustic soda, 200 parts of novolak 1.3 are reacted with 569 parts of ethylene oxide analogously to Example 2.1. The resulting product contains, as the main constituent, a 7-nucleus novolak oxyethylate with on average 54.3 oxyethylene units per molecule and a hydroxyl number of 126.

(2.5) After addition of 1.1 parts of freshly powdered caustic soda, 200 parts of 5-nucleus novolak 1.5 are oxyethylated in a pressure vessel, while stirring and introducing 596 parts of ethylene oxide at 160°-170° C., a pressure of 2-4 bar being maintained. After the ethylene oxide has been forced in, the mixture is subsequently stirred at 160°-170° C. for a further hour. The resulting viscous oxyethylate contains 95 oxyethylene units per molecule and has a hydroxyl number of 51.

(2.6) After addition of 6 parts of sodium methylate (30% strength in methanol), 200 parts of 4-nucleus novolak 1.4 are heated to 70°-80° C. in a pressure vessel flushed with nitrogen gas, with stirring, and the methanol is stripped off under reduced pressure. After the temperature has been increased to 140°-150° C. and the pressure to 2-4 bar, oxyethylation is carried out with 569 parts of ethylene oxide. The resulting viscous oxyethylate contains on average 83.3 oxyethylene units per molecule and has a hydroxyl number of 46.

(2.7) 200 parts of 5-nucleus phenylphenol-novolak 1.6 are taken in a pressure vessel and melted. After addition of 2 parts of freshly powdered sodium hydroxide, oxyethylation is carried out with 579 parts of ethylene oxide under a nitrogen atmosphere analogously to Example 2.6. The resulting viscous green novolak ethylate contains on average 60 oxyethylene units per molecule and has a hydroxyl number of 79.

(2.8) After addition of 9 parts of sodium methylate (30% strength in methanol), 200 parts of 9-nucleus novolak 1.7 are heated to 80°-90° C. in a pressure vessel, with stirring, and the methanol is stripped off under reduced pressure. The internal temperature is increased to 150°-170° C. and 561.3 parts of ethylene oxide are forced in under a pressure of 4-6 bar. The mixture is then stirred at 150°-160° C. for a further hour. The resulting waxy brown resin oxyethylate contains on average 96.3 oxyethylene units per molecule and has a hydroxyl number of 69.

(2.9) After addition of 1.0 part of sodium hydroxide, 200 parts of novolak 1.2 are oxyethylated with 839 parts of ethylene oxide as described in Example 2.1. The resulting product chiefly corresponds to a 9-nucleus novolak oxyethylate with 200 oxyethylene units per molecule and with a hydroxyl number of 47.

(2.10) After addition of 1.0 part of sodium hydroxide, 200 parts of novolak 1.8 are oxyethylated with 419 parts of ethylene oxide as described in Example 2.1. The resulting product chiefly corresponds to a 5-nucleus novolak oxyethylate with 35 oxyethylene units per molecule and with a hydroxyl number of 123.

(2.11) After addition of 1.0 part of powdered caustic soda, 300 parts of novolak 1.9 are reached with 853 parts of ethylene oxide analogously to Example 2.1. The resulting product contains, as the main constituent, a 7-nucleus novolak oxyethylate with on average 67 oxyethylene units per molecule and a hydroxyl number of 98.

3. PREPARATION OF THE ESTERS OF THE OXYALKYLATED NOVOLAKS (3.1) 300 parts of 7-nucleus oxyethylate from Example 2.1 are heated to 70°-80° C. with 58 parts of colophony and the mixture is stirred for one hour under a nitrogen ga. 6 parts of tin powder, 1.5 parts of p-toluenesulfonic acid and 150 ml of xylene are added, the mixture is heated at 150°-160° C. for 16 hours and the water of reaction is removed from the circulation. The xylene is then distilled off. The product has an acid number (DIN 53185) of less than 20. 14.0 parts of maleic anhydride are now added and the mixture is heated at 70°-8020 C. for a further 3 hours, under nitrogen gas. A solution of 18.6 parts of sodium sulfite in 523 parts of water is allowed to run into the resulting maleic acid half-ester product and the mixture is stirred at 70°-80° C. for between 1 and 2 hours until the batch has become clearly water-soluble. The amount of water added with the sodium sulfite solution can be 50-85% by weight of the resulting product solution. The main product is a 7-nucleus novolak oxyethylate mixed ester in which 4 polyoxyethylene chains are esterified with resin acids and 3 are half-esterified with sulfosuccinic acid.

(3.2) 500 parts of 7-nucleus oxyalkylate from Example 2.2 and 71.7 parts of partly hydrogenated colophony are heated together to 70°-80° C. and are thoroughly mixed for one hour, under nitrogen gas. 2.5 parts of p-toluenesulfonic acid, 10 parts of tin powder and 150 ml of xylene are added and the mixture is heated at 150°-160° C. for 16 hours, using a water separator, the water of reaction being continuously removed from the circulation. After the xylene has been distilled off, an acid number of less than 5 is determined. 17 parts of maleic anhydride are then added and the mixture is heated at 70°-80° C. for a further 3 hours, under nitrogen gas. A solution of 22 parts of sodium sulfite and 523 parts of water is then allowed to run in and the mixture is stirred at 70°-80° C. for 1 to 2 hours until the batch has become clearly water-soluble. The amount of water used can be between 50 and 86% of the resulting solution of the product. The main product is a mixed ester of an oxyethylated 7-nucleus novolak in which 4 polyoxyethylene chains are modified terminally with resin acid ester groups and 3 with sulfosuccinic acid half-ester groups.

(3.3) After addition of 37.9 parts of disproportionated colophony, 500 parts of oxyethylate from Example 2.3 are esterified with 2.5 parts of p-toluenesulfonic acid and 10 parts of tin powder analogously to Example 3.1 up to an acid number of 18 and then reacted with 43.1 parts of maleic anhydride and subsequently with a solution of 55.3 parts of sodium sulfite in 500 parts of water. The amount of water used can be between 50 and 85% of the finished product solution. The resulting main product is a mixed ester of an oxyethylated 9-nucleus novolak in which 2 polyoxyethylene chains have terminal resin acid ester groups and 7 polyoxyethylene chains have sulfosuccinic acid half-ester groups.

(3.4) After addition of 94.8 parts of disproportionated colophony, 500 parts of oxyethylate from Example 2.3 are esterified with 2.5 parts of p-toluensulfonic acid and 10 parts of tin powder analogously to Example 3.3 and reacted with 24.6 parts of maleic anhydride and then with 26 parts of sodium bisulfite in 700 parts of water. The mixture is then neutralized with 92.2 parts of a product of triethanolamine and 30 moles of ethylene oxide. The finished product solution can be adjusted to a water content of 50-85% by varying the amount of water used. The main product from the preparation is a mixed ester of an oxyethylated 9-nucleus novolak in which 5 polyoxyethylene chains are esterified with resin acid and 4 polyoxyethylene chains are half-esterified with sulfosuccinic acid.

(3.5) After addition of 37.9 parts of disproportionated colophony and 35.0 parts of oleic acid, 500 parts of oxyethylate 2.3 are esterified in the presence of 2 parts of p-toluenesulfonic acid and 4 parts of tin powder analogously to Example 3.3. The product is then reacted with 30.8 parts of maleic anhydride and subsequently with 39.5 parts of sodium sulfite in b 600 parts of water. The main product is a mixed ester of an oxyethylated 9-nucleus novolak in which 2 polyoxyethylene chains are esterified with resin acid and 2 with oleic acid and 5 are half-esterified with sulfosuccinic acid.

(3.6) 500 parts of oxyethylate from Example 2.6 are esterified with 61 parts of colophony analogously to Example 3.1 and the product is then reacted with 19.7 parts of maleic anhydride and subsequently with 25.3 parts of sodium sulfite in 400 parts of water. The amount of water used can advantageously also be varied so that a water content of between 50 and 85% is established in the solution of the product. The main product is a mixed ester of an oxyethylated 4-nucleus novolak in which 2 polyoxyethylene chains have terminal resin acid ester groups and 2 chains have sulfosuccinic acid half-ester groups.

(3.7) 500 parts of oxyethylate from Example 2.4 are esterified with 141.5 parts of disproportionated colophony analogously to Example 3.1 and the product is then reacted with 61.0 parts of maleic anhydride and subsequently with 78.7 parts of sodium sulfite in 400 parts of water. The main product is mixed ester of an oxyethylated 7-nucleus novolak in which 3 polyoxyethylene chains are esterified with resin acid and 4 polyoxyethylene chains are half-esterified with sulfosuccinic acid.

(3.8) 500 parts of oxyethylate from Example 2.5 are esterified with 45.9 parts of disproportionated colophony analogously to Example 3.1 and the product is then reacted with 22.3 parts of maleic anhydride and subsequently with a solution of 28.7 parts of sodium sulfite in 800 parts of water, it being possible to establish a water content of the finished solution of advantageously between 50 and 80% by weight by varying the amount of water. The main product is a mixed ester of an oxyethylated 5-nucleus novolak in which 2 polyoxyethylene chains are esterified with resin acid and 3 are half-esterified with sulfosuccinic acid.

(3.9) 300 parts of oxyethylate from Example 2.7 are esterified with 51.0 parts of disproportionated colophony, analogously to Example 3.1, and the product is then reacted with 24.9 parts of maleic anhydride and subsequently with 31.9 parts of sodium sulfite (in 500 parts of water). The main product is a mixed ester of an oxyethylated 5-nucleus novolak in which 2 polyoxyethylene chains are terminally modified with resin acid ester groups and 3 are modified with sulfosuccinic acid half-ester groups.

(3.10) 300 parts of oxyethylate from Example 2.8 are esterified with 31.8 parts of commercially available colophony analogously to Example 3.1. A mixture of 14.5 pats of a 2-($C_{12}$-alk-4-enyl)-succinic anhydride and 20.6 parts of maleic anhydride is then added and the mixture is stirred at 70°-80° C. for 3 hours, under nitrogen gas. A solution of 26.5 parts of sodium sulfite in 400 parts of water is then allowed to run at 80°-90° C. and the mixture is stirred at 70°-80° C. for 1 to 2 hours until the batch is clearly water-soluble. The resulting solution of the product can have a water content of between 50 and 80% by varying the amount of water used. The main product is a mixed ester of an oxyethylated 7-nucleus novolak in which 2 polyoxyalkylene chains are esterified with resin acid, one chain is half-esterified with an alkenylsuccinic acid and 4 chains are half-esterified with sulfosuccinic acid.

(3.11) 300 parts of oxyethylate from Example 2.1 and 43.5 parts of disproportionated colophony are reacted analogously to Example 3.1. After addition of 250 ml of methylene chloride, 22.4 parts of chlorosulfuonic acid are added dropwise at 15°-20° C., a weak stream of dry nitrogen gas being passed through the solution and the hydrogen chloride formed thus being removed. Towards the end of the reaction, the mixture is heated to 30° C. and stirred until no further hydrogen chloride gas escapes. The methylene chloride is distilled off under reduced pressure at about 30° C. and first 400 parts of water and then, for neutralization, 23.1 parts of 33% strength sodium hydroxide solution are added dropwise. The water content of the finished solution of the product should be between 50 and 85%.

The product is a mixed ester of an oxyethylated 7-nucleus novolak in which 3 polyoxyethylene chains are esterified with resin acid and 4 with sulfuric acid.

(3.12) 37.9 parts of disproportionated colophony are added to 500 parts of oxyethylate from Example 2.3, esterification is carried out in accordance with Example 3.1 with 2.5 parts of p-toluenesulfonic acid and 10 parts of tin powder up to an acid number of 16 and the product is then reacted with 65 parts of phthalic anhydride in the presence of 0.5 parts of powered caustic soda at 80°-90° C. in the course of 5 hours. A water content of 65% is established in the finished solution by addition of 1,117 parts of water. The product is a mixed ester of an oxyethylated 9-nucleus novolak in which 2 polyoxyethylene chains are esterified with resin acid and 7 are half-esterified with phthalic acid.

(3.13) 300 parts of oxyethylate from Example 2.9 are heated to 70°-80° C. with 74.8 parts of colophony and the mixture is stirred for one hour, under nitrogen gas. 10 parts of tin powder, 1.5 parts of p-toluenesulfonic acid and 150 ml of xylene are added, the mixture is heated at 150°-160° C. for 16 hours and the water of reaction is removed from the circulation. The xylene is then distilled off. The product has an acid number (DIN 53185) of less than 20 and contains, as the main product, an ester of the oxyethylated 3-nucleus novolak in which the 9 polyoxyethylene chains are terminally esterified with resin acid groups.

(3.14) After addition of 41.6 parts of disproportionated colophony, 300 parts of oxyethylate from Example 2.9 are esterified analogously to Example (3.13) with 1.5 parts of p-toluenesulfonic acid and 10 parts of tin powder up to an acid number of 19. In the resulting main product, of 9 polyoxyethylene chains, 5 terminal hydroxyl groups are esterified with resin acid.

(3.15) After addition of 79.1 parts of disproportionated colophony, 300 parts of oxyethylate from Example 2.10 are esterified analogously to Example (3.13) with 1.5 parts of p-toluenesulfonic acid and 10 parts of tin powder up to an acid number of 18. In the resulting main product, of 5 polyoxyethylene chains 2 are terminally esterified with resin acid.

(3.16) 500 parts of oxyethylate from Example 2.11 are esterified with 113 parts of disproportionated colophony analogously to Example 3.1 and the product is then reacted with 48.9 parts of maleic anhydride and subsequently with 62.9 parts of sodium sulfite in 400 parts of water. The main product is a mixed ester of an oxyethylated 7-nucleus novolak in which 3 polyoxyethylene chains are esterified with resin acid and 4 polyoxyethylene chains are half-esterified with sulfosuccinic acid.

4. USE EXAMPLE (4.1) 1,012 parts of 3,3'-dichloro-4,4'-diamino-diphenyl are stirred with 6,000 parts of water and 2,500 parts by volume of 30% strength hydrochloric acid and then bisdiazotized with 1,052 parts by volume of 40% strength sodium nitrite solution at 0°-15° C. For preparation for the coupling reaction, 1,466 parts of acetoacetylaminobenzene are dissolved in 10,000 parts of water and 800 parts by volume of 33% strength sodium hydroxide solution, 160 parts of the surfactant prepared according to Example 3.3 are added and a precipitate is obtained by addition of 700 parts by volume of 80% strength acetic acid. The azo coupling is carried out with slow introduction of the prepared solution of the bis-diazonium salt to the suspension of the precipitated coupling component, the pH being kept at about 4.5 by continuous addition of 6% strength sodium hydroxide solution. When the coupling has ended, the acetic acid suspension is heated to 50° C. and 150 parts of dodecyl-benzyl-dimethylammonium chloride, 750 parts of tallow fat propylenediamine and 300 parts of bis-(4-aminocyclohexyl)-methane are added. The mixture is heated to 90°-100° C. and this temperature is maintained for half an hour. The mixture is then rendered alkaline with 1,5000 parts by volume of 33% strength sodium hydroxide solution and is stirred at 90°-100° C. for a few hours. The product is then filtered, washed, dried and ground. A preparation of C.I. Pigment Yellow 12 which can readily be used for pigmenting gravure printing inks based on toluene is obtained. Reddish-tinged yellow gravure printing inks which show very good results in respect of depth of color, gloss, transparency and gradation properties are obtained with the pigment preparation. The gravure printing inks pigmented with these are also distinguished by an advantageously low viscosity.

(4.2) If the procedure is as in Example 1, but the surfactant from Example 3.3 is replaced by the surfactant from Example 3.5, a pigment preparation of Pigment Yellow 12 with similarly advantageous properties is obtained.

(4.3) Comparison example analogous to Example 1 of EP-A-0,057,880 for the manufacture of a pigment preparation for gravure printing inks based on toluene: if the procedure is as in Example 4.1 or Example 4.2 but the surfactant from Example 3.3 or 3.5 is replaced by 160 parts of oleylamine acetate, a pigment preparation of Pigment Yellow 12 which shows distinctly poorer results in respect of depth of color, gradation properties, gloss and transparency in gravure printing inks in comparison with Example 4.1 and Example 4.2 is obtained.

(4.4) 1,396 parts of 1-acetoacetylamino-2,4-dimethylbenzene and 341 parts of 1-acetoacetylamino-2-methoxybenzene are dissolved in 10,000 parts of water and 830 parts by volume of 33% strength sodium hydroxide solution. This solution is brought to 10° C. with ice and 40 parts by volume of a 10% strength solution of the product (100% pure) from Example 3.8 are added. The coupling component is then precipitated with 1,140 parts by volume of 50% strength acetic acid. Coupling is carried out by slowly introducing a bis-diazonium salt solution, which has been prepared analogously to Example 4.1, to the suspension of the precipitated coupling component, the pH being kept at about 4.5 with 6% strength sodium hydroxide solution. When the coupling has ended, 1,100 parts by volume of 33% strength sodium hydroxide solution and a hot solution. at 80° C., consisting of 750 parts of a balsam resin, 4,000 parts by volume of water and 220 parts by volume of 33% strength sodium hydroxide solution are added to the pigment suspension. The mixture is heated to 98° C., this temperature is maintained for 2 hours and 2,000 parts by volume of normal hydrochloric acid are then added. The product is then filtered off, washed and dried. A pigment preparation which is outstandingly suitable for incorporation into graphic printing inks is obtained. The printing inks thus pigmented are distinguished by a good depth of color and a high transparency.

(4.5) If the procedure is as in Example 4.4 but the product from Example 3.10 is used instead of the product from Example 3.8, a pigment preparation with a similarly advantageous quality to that described under 4.4 is obtained.

(4.6) Comparison Example: If the procedure is as described in Example 4.4 or Example 4.5 but 40 parts by volume of a 10% strength solution of a commercially available coupling auxiliary based on an alkyl polyglycol ether is used instead of 40 parts by volume of a 10% strength solution of compound 3.8 or 3.10, a pigment preparation which has a distinctly reduced depth of color and noticeably reduced transparency in graphic printing inks in comparison with the pigment preparations described in Example 4.4 or 4.5 is obtained.

(4.7) 11 parts of dinitroaniline are diazotized in a known manner in a mixture of sulfuric acid and hydrochloric acid with 10.4 parts of 40% strength sodium nitrite solution. Parallel to this, 8.64 parts of 2-naphthol are dissolved in a mixture of 8.8 parts of 33% strength sodium hydroxide solution and 100 parts of water. The 2-naphthol is precipitated again by adding the resulting solution dropwise to a mixture of one part of the surfactant from Example 3.6, 300 parts of water and 10 parts of 31% strength hydrochloric acid. Azo coupling to give C.I. Pigment Orange 5 is then carried out in a known manner by introduction of the clarified diazonium salt solution to the suspension of the precipitated 2-naphthol. The pigment is then filtered, washed with water and finally dried. The resulting pigment is distinguished by a high tinctorial strength both in letterpress or offset printing and in aqueous preparations for flexographic printing inks or emulsion paints. The printing inks and preparations have an advantageously low viscosity. The resulting pigment shows a good gloss and transparency in letterpress and offset printing.

(4.8) If the procedure is as in Example 4.7 but the surfactant from Example 3.6 is replaced by the surfactant from Example 3.7, a Pigment Orange 5 of a similarly advantageous quality is obtained.

(4.9) Comparison Example: If the procedure is as in Example 4.7 but the pigment is prepared without the surfactant from Example 3.6 or Example 3.7, a pigment which shows a substantially poorer tinctorial strength, poorer gloss and poorer transparency in letterpress and offset printing in comparison with the pigment prepared according to Example 4.7 or 4.8 is obtained. Only a lower tinctorial strength and a lower brilliancy of the prints is also achieved in the flexographic printing inks or emulsion paints prepared for comparison.

(4.10) 50 parts of Pigment Yellow 83 (C.I. No. 21108) are ground with 15 parts of a 43% strength aqueous solution of the surfactant according to Example 3.3 and also 25 parts of ethylene glycol and 14 parts of water in a stirred bead mill with $\phi$ 1 m siliquartzite glass beads until the required fine division is reached. A further 22 parts of water are then added to the ground material and the mobile pigment dispersion is separated from the grinding bodies via a sieve. The 40% strength pigment dispersion can be diluted with water in all proportions and is particularly suitable for coloring aqueous binder systems.

(4.11) 50 parts of C.I. Pigment Red 9 (Color Index No. 12460) are ground with 14 parts of a 39% strength aqueous solution of the surfactant from Example 3.6, 23 parts of ethylene glycol and 1 5parts of water in a stirred bead mill with $\phi$ 1 mm siliquartzite glass beads and the ground material is then diluted with 10 parts of water. The resulting mobile pigment dispersion is outstandingly suitable for coloring aqueous flexographic and gravure printing inks and for pigmenting aqueous paints based on dispersions of plastics.

(4.12) 50 parts of C.I. Pigment Blue 15 (C.I. No. 74160), 20 parts of a 39% strength aqueous solution of the surfactant from Preparation Example 3.6, 150 parts of ethylene glycol and 115 parts of water are ground in a stirred bead mill with 1 mm siliquartzite glass beads and the ground material is then diluted by addition of 40 parts of water. The pigment dispersion with very good flow properties obtained in this manner is outstandingly suitable for use in aqueous flexographic and gravure printing inks.

(4.13) 50 parts of the disperse dyestuff 2-methyl-3-ethoxycarbonyl-6-morpholino-10-oxypyrazolo(2,3b-)benzo(d,e)isoquinoline are ground with 40 parts of the compound prepared from Example 3.3 and 110 parts of water in a stirred bead mill for 4 hours until fine division is achieved. After addition of 50 parts of water, a 20% strength color paste which is very finely divided and meets all the coloristic requirements, in particular for dyeing polyester and polyester/wool and polyester/viscose staple fiber blended yarns, is obtained. Similarly good results are obtained when the compound from Example 3.1, 3.5 or 3.8 is used.

(4.14) 50 parts of the disperse dyestuff 4-(2-chloro-4-nitrphenylazo)-3-methyl-N-ethyl-N-(2-cyanoethyl)-aniline are ground with 40 parts of the surfactant from Example 3.1 and 110 parts of water in the course of 3 hours until fine division is achieved. The resulting dispersion is brought to a dyestuff content of 30% by addition of further strength standardizing agent and is dried to a powder in a spray-dryer. The dyestuff powder has very good coloristic and dyeing properties. Similarly good results are obtained if the surfactant from Example 3.3 or Example 3.5 is used instead of the surfactant from Example 3.1 used.

(4.15) 100 parts of the plant protection agent 2-carbomethoxyamino-benzimidazole are ground with 10 parts of the surfactant from Example 3.9 and 10 parts of the surfactant from Example 3.10 as well as 76 parts of water in a stirred mill for 2 hours until fine division is achieved. After the grinding bodies have been removed, a very stable dispersion with a good suspendability and without a sediment is obtained.

(4.16) 73.9 parts of methylnaphthalene are homogeneously stirred with 75 parts of the 35% strength formulation from Example 3.2. The concentrate is then made up to 1,000 parts by volume with water. A finely disperse carrier emulsion which has an outstanding stability at the dilution usually employed (1:10) and can be used for a relatively long time is obtained.

We claim:

1. A resin acid ester of the formula (1)

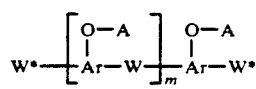

(1)

wherein the radical Ar, independently of one another is an aromatic ring system which is unsubstituted or substituted by one or more radicals from the group consisting of saturated or unsaturated $C_1-C_{18}$-alkyl, $C_1-C_{18}$-alkoxy, $C_2-C_5$-alkanoyl, $C_6-C_{10}$-aryl and $(C_6-C_{10}$-aryl)-$C_1-C_4$-alkyl;

the radical A, independently of one another is a group of the formula $-(X-O)_n-Y$, in which n is an integer from 1 to 150 wherein the radical X, independently of one another is a group of the formula $-CH_2CH_2-$, $-CH_2CH(CH_3)-$ or $-CH(CH)C-H_2-$, (a) all the radicals Y are the acyl radical of a non-modified or of a modified natural resin acid, or (b) 10% to 50% of the radicals Y are the acyl radical of a non-modified or of a modified natural resin acid and 90% to 50% of the radicals Y, in each case independently of one another, are a radical or various radicals selected from the group consisting of hydrogen, the acyl radical of a saturated carboxylic acid with 1 to 24 carbon atoms, the acyl radical of an unsaturated carboxylic acid with 3-24 carbon atoms, the acyl radical of a hydroxy carboxylic acid with 2-24 carbon atoms, the acyl radical of an alkyl-, alkenyl- or alkylidenesuccinic acid with 8-18 carbon atoms in the side chain, and an acyl radical of the formulae $-CO-CH=CH-COOM$, $-COCH_2CH(SO_3M)-COOM$, $-CO-(CH_2)_p-COOM$, $-CO-C_6H_4-COOM$ and $-SO_3M$, wherein p is a number from 0 to 14 and M is a cation;

the radical W, independently of one another, is a divalent group of the formula $-CHR-$ or $-CHR-N(R^*)-T-N(R^*)-CHR-$, wherein the radical $R^*$, independently of one another, is hydrogen, $C_1-C_4$-alkyl, $C_2-C_4$-hydroxyalkyl, a radical of the formula A or $-Q-O-A$, wherein Q is a $C_2-C_4$-alkylene group, R, independently of one another, is hydrogen or $C_1-C_9$-alkyl, and T, independently of one another, is $C_2-C_{12}$-alkylene or $C_2-C_{12}$-alkylene which is interrupted by at least one of the divalent groups $-O-$ or $-NR'-$, which do not stand side by side and wherein R' is hydrogen, $C_1-C_4$-alkyl, $C_2-C_4$-hydroxyalkyl, A or $-Q-O-A$; the radical $W^*$, independently of one another, is hydrogen or a group of the formula $-CHR-N(R^*)-T-N(R^*)A$; and m is an integer from 1 to 16.

2. The resin acid ester of claim 1, in which Ar is benzene, naphthalene or biphenyl radical which is unsubstituted or substituted by a $C_1-C_{12}$-alkyl radical or by acetyl.

3. The resin acid ester of claim 1, in which Y is an acyl radical of the formula $-CO-CH=CH-COOM$ or $-CO-CH_2-CH(SO_3M)-COOM$ or a mixture thereof, wherein M is an alkali metal, one equivalent of an alkaline earth metal, unsubstituted ammonium, an ammonium group substituted by 1-4 $C_1-C_4$-alkyl or $C_1-C_4$-hydroxyalkyl, or an ammonium group obtained by addition of up to 150 units of ethylene oxide or propylene oxide or both onto ammonia or onto a mono-, di- or trialkylamine with 1-4 carbon atoms in the alkyl radical.

4. The resin acid ester of claim 1, in which W is the group $-CHR-$, X is the group $-CH_2CH_2-$, $W^*$ is hydrogen or a group of the formula $-CHR-NA-T-NA_2$, n ranges from 1 to 50 and m ranges from 3 to 8.

5. The resin acid ester of claim 1, in which 20% to 40% of the radicals Y are the acyl radical of a non-modified or modified natural resin acid, 0% to 40% of the radicals Y are the acyl radical of a saturated or unsaturated fatty acid with 8 to 18 carbon atoms, an acyl radical of an alkyl-, alkenyl- or alkylidenesuccinic acid with 8 to 18 carbon atoms in the side chain, hydrogen or a mixture thereof, and 80% to 20% of the radicals Y are a half-ester group of maleic acid, sulfosuccinic acid, phthalic acid or sulfuric acid, the percentages of the radicals summing to 100%.

* * * * *

UNITED STATES PATENT AND TRADEMARK OFFICE
CERTIFICATE OF CORRECTION

PATENT NO. : 5,100,989

DATED : March 31, 1992

INVENTOR(S) : Heinz Uhrig, Erich Ackermann and Reinhold Deubel

It is certified that error appears in the above-identified patent and that said Letters Patent is hereby corrected as shown below:

At column 1, line 21, "ponent," should read --ponents,--.

At column 1, line 36, "moveover" should read --moreover--.

At column 1, line 47, "ad" should read --and--.

At column 2, line 9, after "preferably" insert --10-5% of the radicals Y, in each case independently of--.

At column 2, line 16, after "atoms" insert --or--.

At column 3, line 20, "radials" should read --radicals--.

At column 5, line 14, strike "b" appearing after "and".

At column 5, line 27, "oxtyl-" should read --octyl- --.

At column 6, line 10, "1340°" should read --140°--.

UNITED STATES PATENT AND TRADEMARK OFFICE
CERTIFICATE OF CORRECTION

PATENT NO. : 5,100,989

DATED : March 31, 1992

INVENTOR(S) : Heinz Uhrig, Erich Ackermann and Reinhold Deubel

It is certified that error appears in the above-identified patent and that said Letters Patent is hereby corrected as shown below:

At column 6, line 19, "its" should read --is--.

At column 6, line 25, "0.05-2.0%" should read --0.05-1.0%--.

At column 6, line 27, "to" should read --out--.

At column 6, line 31, after "is" insert --as--.

At column 6, line 54, "2-chloro-1-naphtol" should read --2-chloro-1-naphthol--.

At column 7, line 35, "steric" should read --stearic--.

At column 7, line 49, "he" should read --the--.

At column 9, line 61, "move-" should read --more- --.

At column 9, line 62, "sin" should read --in--.

At column 10, line 14, "nonylphenols" should read --nonylphenol--.

UNITED STATES PATENT AND TRADEMARK OFFICE
CERTIFICATE OF CORRECTION

PATENT NO. : 5,100,989

DATED : March 31, 1992

INVENTOR(S) : Heinz Uhrig, Erich Ackermann and Reinhold Deubel

It is certified that error appears in the above-identified patent and that said Letters Patent is hereby corrected as shown below:

At column 10, line 48, "if" should read --is--.

At column 10, line 49, "9°" should read --90°- --.

At column 11, line 21, "dodecylenzenesulfonic" should read --dodecylbenzenesulfonic--.

At column 11, line 23, "t" should read --to--.

At column 11, line 57, "13.3" should read --173.3--.

At column 12, line 16, "ha" should read --has--.

At column 13, line 20, "reached" should read --reacted--.

At column 13, line 32, "ga" should read --gas--.

At column 13, line 39, "8020" should read --80°--.

UNITED STATES PATENT AND TRADEMARK OFFICE
CERTIFICATE OF CORRECTION

PATENT NO. : 5,100,989

DATED : March 31, 1992

INVENTOR(S) : Heinz Uhrig, Erich Ackermann and Reinhold Deubel

It is certified that error appears in the above-identified patent and that said Letters Patent is hereby corrected as shown below:

At column 13, line 66, "86%" should read --85%--.

At column 14, line 38, strike "b" appearing before "600".

At column 15, line 22, "pats" should read --parts--.

At column 15, line 39, "chlorosulfuonic" should read --chlorosulfonic--.

At column 16, line 60, "1,5000" should read -1,500--.

At column 17, line 10, after "0,057,880" insert --(U.S. -A- 4,515,639)--.

At column 18, line 44 "1 5parts" should read --15 parts--.

UNITED STATES PATENT AND TRADEMARK OFFICE
CERTIFICATE OF CORRECTION

PATENT NO. : 5,100,989

DATED : March 31, 1992

INVENTOR(S) : Heinz Uhrig, Erich Ackermann and Reinhold Deubel

It is certified that error appears in the above-identified patent and that said Letters Patent is hereby corrected as shown below:

In claim 1, at column 19, lines 50-51, the subscript 3 is missing in the last formula, which should read:

-- $-CH(CH_3)CH_2-$ --.

Signed and Sealed this

Sixth Day of July, 1993

Attest:

MICHAEL K. KIRK

*Attesting Officer*  Acting Commissioner of Patents and Trademarks